United States Patent
Wismer

(10) Patent No.: US 6,605,193 B2
(45) Date of Patent: Aug. 12, 2003

(54) RECOVERY OF HFC-32

(75) Inventor: John A. Wismer, Lower Makefield, PA (US)

(73) Assignee: Atofina Chemicals, Inc., Philadelphia, PA (US)

( * ) Notice: Subject to any disclaimer, the term of this patent is extended or adjusted under 35 U.S.C. 154(b) by 38 days.

(21) Appl. No.: 09/841,909

(22) Filed: Apr. 25, 2001

(65) Prior Publication Data

US 2002/0157938 A1 Oct. 31, 2002

(51) Int. Cl.$^7$ .............. B01D 3/34; C01B 7/19; C07C 17/386
(52) U.S. Cl. .............. 203/57; 203/78; 203/80; 423/483; 423/484; 423/488; 570/178
(58) Field of Search .............. 203/73, 78, 80, 203/57; 423/483, 488, 484; 570/178, 177

(56) References Cited

U.S. PATENT DOCUMENTS

| 3,101,304 | A | | 8/1963 | Wiist ..................... 203/67 |
| 5,523,015 | A | | 6/1996 | Tsuda et al. ............ 252/171 |
| 5,707,497 | A | | 1/1998 | Galland et al. ........... 203/75 |
| 6,166,275 | A | * | 12/2000 | Cerri et al. .............. 570/165 |
| 6,365,580 | B1 | * | 4/2002 | Clemmer et al. ......... 514/134 |

FOREIGN PATENT DOCUMENTS

| JP | 07033691 | * | 2/1995 |
| WO | WO 97/03936 | | 2/1997 |
| WO | WO 99/07660 | | 2/1999 |
| WO | 99/25670 | * | 5/1999 |

* cited by examiner

*Primary Examiner*—Virginia Manoharan
(74) *Attorney, Agent, or Firm*—William D. Mitchell

(57) ABSTRACT

A method for isolating 32 from a crude mixture containing HCl and an azeotropic mixture of 32 and HF is provided without the need to isolate any HF azeotrope.

3 Claims, No Drawings

RECOVERY OF HFC-32

BACKGROUND OF THE INVENTION

This invention relates to a method for isolating difluoromethane ("HFC-32" or "32") from a crude mixture containing hydrogen chloride ("HCl") and an azeotropic mixture of 32 and hydrogen fluoride ("HF"), particularly, as part of a process wherein 32 is being manufactured by reacting methylene chloride ("30") and HF, such reaction normally being conducted in the gas phase. The reactor effluent from such reactions mostly comprises 32, unreacted 30 and HF, by-product HCl and an intermediate product chlorofluoromethane ("31"). HFC-32 is a known refrigerant and is typically used blended together with other refrigerants, such as pentafluoroethane ("HFC-125").

A number of schemes have been proposed for purifying the 32 contained in this reactor effluent, some of which cite a low HF concentration azeotrope with 32 as precluding isolation of 32 by straight distillation. In U.S. Pat. No. 5,707,497, the azeotrope is broken by pressure swing distillation. In U.S. Pat. No. 5,523,015, the azeotrope is broken by phase separation. Both of these methods require a substantial investment and isolation of HF azeotropes. It would be useful to have a scheme for isolation of 32 which does not require isolation of an azeotrope.

BRIEF SUMMARY OF THE INVENTION

A method of isolating 32 from a crude mixture containing HCl and an azeotropic mixture of 32 and HF is provided, which method comprises the steps of (A) distilling said crude mixture in a column with a cofeed of a compound (preferably 30) having a boiling point higher than that of 32 in order to generate a column overhead of HCl and a column bottoms whose bubble point and composition varies with the amount of heat applied to it, (B) removing HF from the column bottoms of step (A) by washing, and (C) distilling the remaining mixture from step (B) to separate 32 from higher boiling compounds. The higher boiling compounds from step (C) are preferably recycled to the column of step (A). As described in more detail below, the "washing" referred to in step (B) encompasses both absorbing into water and neutralizing with aqueous caustic.

DETAILED DESCRIPTION

It has now been found that the above scheme offers several advantages over previous separation techniques, such as (1) clean, anhydrous HCl is obtained by distillation in step (A); (2) the yield loss of HF associated with the process is limited to that associated with the 32/HF azeotrope despite never isolating the azeotrope; (3) any unreacted HF and 30, along with intermediate 31, in the reactor effluent can be recovered for recycle to the reactor at the beginning of the separation train, prior to step (A), by distillation, thus avoiding contamination by downstream equipment and allowing materials of construction requirements to be relaxed, and (4) distillation control of the HCl column in step (A) is enhanced by allowing the reboiler to operate on bubble point control. If the reboiler contained an azeotrope, the temperature and compositon of the bottoms would be invariant regardless of the heat supplied to the reboiler, making it difficult to control the heat input to the column. Since the HCl column operates under constant pressure, "bubble point" as used herein refers to the temperature at which a chemical mixture starts to boil; it is called a bubble point because the boiling temperature will start to increase immediately as the mixture starts boiling provided it is not azeotropic, so that there is no boiling point in the common sense of the word.

The pressure of the HCl column is typically in the 100 psig to 500 psig range. At pressures of 210 psig, the overhead temperature would be about −19° C., depending on the amount of any minor impurities. The HCl column bottoms is a mixture whose bubble point depends on the amount and composition of the high boiling cofeed and any recycle from step (C). The principal determinants for a preferred high boiling cofeed (or cofeeds) are that it (or they) be significantly less volatile than 32, chemically inert in the system, thermally stable, and have a low enough boiling point to give a reasonable bubble point at the bottom of the column in step (C). A preferred boiling point range for the cofeed(s) is −30° C. to +70° C. Preferred compounds are chlorocarbons, hydrochlorofluorocarbons or hydrofluorocarbons containing 1 to 4 carbons. Particularly preferred is 30 since it is employed as a feedstock in the process.

Acid wash step (B) can employ conventional techniques. For example, the stream from step (A) can either be vaporized into a low pressure water absorber/caustic scrubber system or scrubbed by an aqueous base under pressure in a liquid phase mixer/settler system. If scrubbed in a gas phase system, it would first be dried and compressed before feeding a high pressure distillation. If a high pressure liquid system is used, simple drying would suffice before feeding the distillation system. The effluent from the wash system is then fed to the final distillation column of step (C), which is normally operated at a pressure similar to that used for the HCl column.

I claim:

1. A method of isolating difluoromethane from a crude mixture containing HCl and an azeotropic mixture of difluoromethane and HF, which method comprises the steps of (A) feeding to a column a stream of said crude mixture and a stream of a compound having a boiling point higher than that of difluoromethane, (B) distilling in said column the streams from step (A) in order to generate a column overhead of HCl and a column bottoms whose bubble point and composition varies with the amount of heat applied to it, (C) removing HF from the column bottoms of step (B) by washing, and (D) distilling the remaining mixture from step (C) to separate difluoromethane from any compound having a boiling point higher than that of difluoromethane without the need to isolate any azeotropic mixture of difluoromethane and HF.

2. A method as in claim 1 wherein any higher boiling compound from step (D) is recycled to the column of step (A).

3. A method as in claim 1 wherein the stream of a compound having a boiling point higher than that of difluoromethane is a stream of methylene chloride.

* * * * *